United States Patent [19]
Goldenberg et al.

[11] Patent Number: 5,352,198
[45] Date of Patent: Oct. 4, 1994

[54] LOCKING CATHETER SYSTEM

[75] Inventors: Barry Goldenberg, Arlington Heights; Jeffrey T. Williams, Grayslake; David Schucart, Homewood; Paul H. Hubbard, Chicago; Lev Melinyshyn, Buffalo Grove, all of Ill.

[73] Assignee: Uresil Corporation, Skokie, Ill.

[21] Appl. No.: 157,648

[22] Filed: Nov. 24, 1993

[51] Int. Cl.⁵ .................. A61M 37/00; A61M 29/00; A61M 5/32
[52] U.S. Cl. .................................. 604/95; 604/178; 604/107
[58] Field of Search .............. 604/95, 104–109, 604/174, 175, 178, 280, 283

[56] References Cited

U.S. PATENT DOCUMENTS

| | | | |
|---|---|---|---|
| 1,207,479 | 12/1916 | Bisgaard | 604/95 X |
| 3,924,633 | 12/1975 | Cook et al. | 604/95 X |
| 4,402,307 | 9/1983 | Hanson et al. | 604/95 X |
| 4,740,195 | 4/1988 | Lanciano | 604/95 |
| 4,807,626 | 2/1989 | McGirr | 604/107 X |
| 4,861,336 | 8/1989 | Helzel | 604/95 |
| 4,869,719 | 9/1989 | Hogan | 604/174 |
| 5,041,085 | 8/1991 | Osborne et al. | 604/51 |
| 5,213,575 | 5/1993 | Scotti | 604/95 |
| 5,215,530 | 6/1993 | Hogan | 604/174 |

*Primary Examiner*—John D. Yasko
*Assistant Examiner*—Adam J. Cermak
*Attorney, Agent, or Firm*—Laff, Whitesel, Conte & Saret

[57] ABSTRACT

A locking catheter system including a flexible catheter having a restraining portion such as a pigtail, malecot rib or J-curve at its distal end and a flexible filament extending therefrom to attaching means at the other end of the catheter. The attaching means comprise a self-sealing sleeve through which the filament passes and an elastomeric sheath which encapsulates the sleeve to restrain the filament.

19 Claims, 2 Drawing Sheets

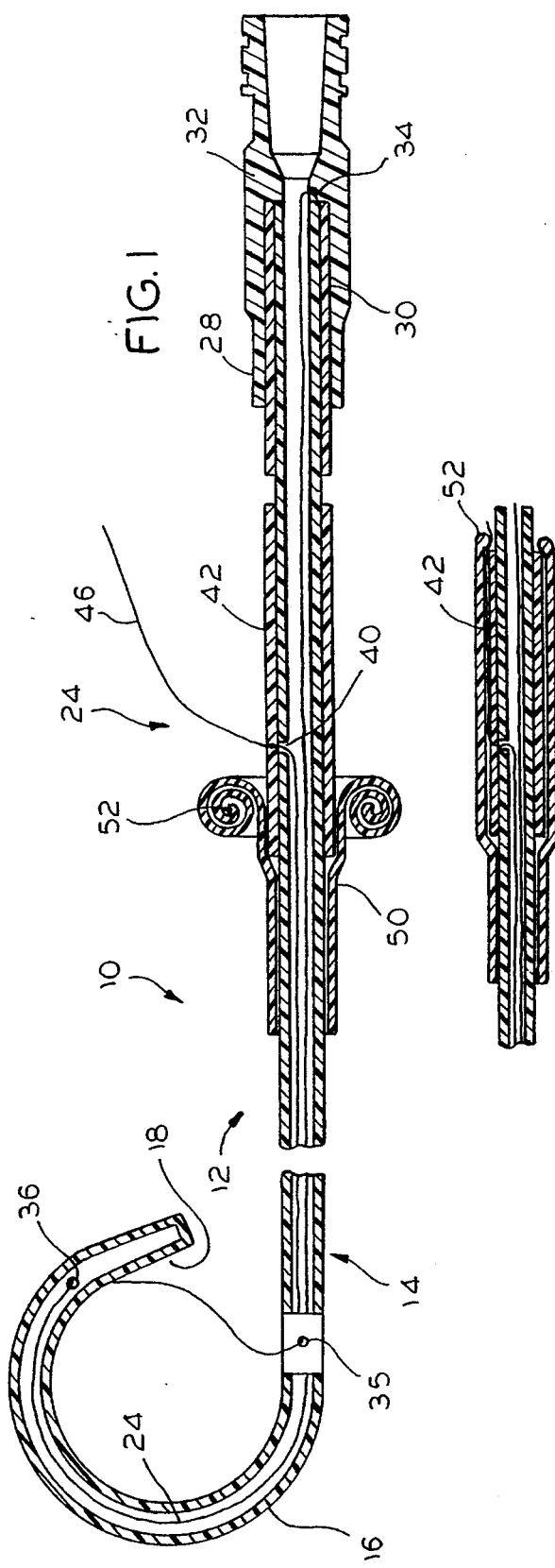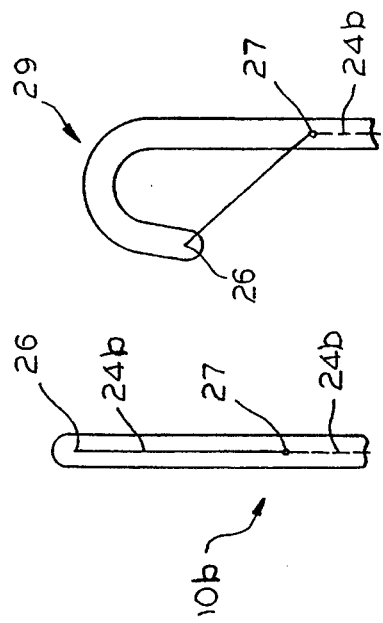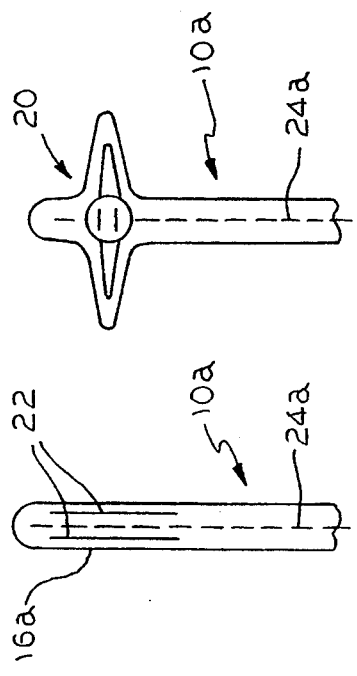

LOCKING CATHETER SYSTEM

BACKGROUND OF THE INVENTION

This invention relates generally to medical (including veterinary) catheters and, more particularly, to a unique medical catheter designed to be removably anchored within a body cavity by forming and maintaining an obstruction to removal in the form of a restraining portion in the distal end of the catheter until it is desired to withdraw the catheter from the cavity.

Flexible catheters are widely used for percutaneous drainage of fluid collections and percutaneous nephrostomy. They are also used for drainage of abscesses, cysts, pleural effusions, empyemas, and other mediastinal collections. In such applications, the catheters are typically inserted either over a previously emplaced guide wire or by direct puncture using a trocar stylet.

Once in position in a body cavity, it is desirable to anchor the catheter before drainage begins. This may be done by forming a restraining portion in the distal end of the catheter in the form of a pigtail, a J-curve or a malecot rib. In order to reliably anchor and then later easily remove the catheter, it is important to be able to lock and unlock the restraining portion in the distal end of the catheter from the proximal end of the catheter, where it protrudes from the body.

One technique for locking a pigtail in the distal end of a drainage catheter is described in U.S. Pat. No. 4,740,195 to Lanciano. That patent describes a suture attached to the distal end of the catheter which is held in position in a stopcock-type of locking mechanism in its proximal end. Another prior art device for locking a pigtail in the distal end of a drainage catheter with a suture arrangement uses a latex sleeve to cover the suture as it exits from a hole the wall of the catheter at its proximal end to thereby holds it in place and also reduce leakage. Both of these prior art techniques are unsatisfactory since they permit liquid leakage along the suture as it emerges from the catheter and gas leakage at the hole in the wall of the catheter.

SUMMARY OF THE INVENTION

The present invention comprises a locking catheter system with a flexible catheter having a locking mechanism at its proximal end and a restraining portion at its distal end. The restraining portion may be a pigtail, a J-curve or a malecot rib. Means, in the form of a flexible filament such as a suture extends from the restraining portion of the catheter to the proximal end of the catheter for drawing the distal end of the catheter toward the proximal end to form or manipulate the restraining portion. Ideally, the flexible filament is non-woven and non-porous.

The heart of the invention lies in means, located at the proximal end of the catheter, for removably attaching the proximal end of the flexible filament to the catheter in a way which is secure, convenient and largely free of leakage. The attaching means include a latex sleeve or other suitable elastomeric self-sealing material which covers a portion of the proximal end of the elongated portion of the flexible cannula. The flexible filament portion emerges from the catheter through the catheter wall beneath the sleeve and then passes through the latex sleeve. A sheath made of silicone or other suitable elastomeric material is provided for encapsulating the latex sleeve once the filament is in the desired position, to thereby lock the restraining portion of the catheter in the desired position and minimize contamination of the suture.

Due to the self-sealing properties of latex, liquid and gaseous leakage from the catheter is minimized by the latex sleeve. The silicone sheath further insures that no leakage will occur, while also preventing problems with the patient related to latex sensitivity. A further advantage of the silicone sheath is that, when stored with the sheath encapsulating the sleeve, deterioration of the latex is slowed, thereby extending the shelf-life of the latex sleeve.

BRIEF DESCRIPTION OF THE DRAWING

The features of this invention which are believed to be novel are set forth with particularity in the appended claims. The invention, together with its objects and advantages, may be best understood by reference to the following description, taken in conjunction with the following drawings, in which like reference numerals identify like elements in the several figures, and in which:

FIG. 1 is a elevation view of the catheter of the invention, cut-away to show the flexible filament positioned therein;

FIG. 1A is a partial cut-away elevation view of the silicone sheath of the catheter in its fully unrolled position;

FIGS. 2A and 2B are diagrammatic representations of a restraining portion in the form of a malecot rib;

FIGS. 3A and 3B are diagrammatic representations of the invention showing the restraining means in the form of a J-curve;

DESCRIPTION OF THE PREFERRED EMBODIMENT

Figure 4A:
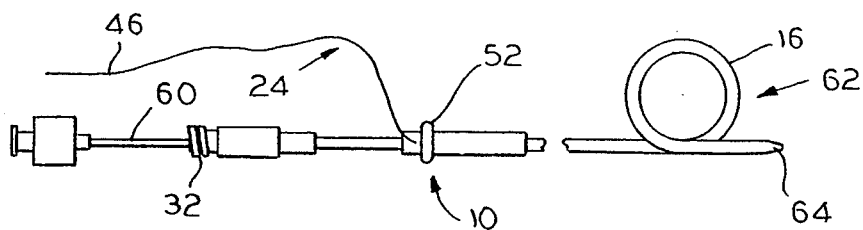
FIGS. 4A and 4B are elevation views of the catheter with pigtail restraining means of the invention illustrating insertion of the catheter over a stiffening cannula into the catheter.

Turning now to FIG. 1, there is depicted a hollow thermoplastic catheter 10 having a proximal end 12, a distal end 14 and a restraining portion 16. The restraining portion of the catheter includes at least one drainage hole 18. Catheter 10 may be made of polyurethane, polyethylene, EVA, nylon, or any other suitable flexible biomaterial. The respective length of the elongated portion and the restraining portion may vary, according to the desired application.

Restraining portion 16 is depicted in FIG. 1 as a pigtail which was preformed in the distal end of the catheter. Other restraining means may be used, such as the malecot rib fixation 20 depicted in FIG. 2B. As seen in FIG. 2A, longitudinal slits 22 are located in the restraining portion 16a of the catheter 10a, so that, as suture 24a is drawn proximally, a malecot rib 20 is formed (FIG. 2B).

Another restraining means is depicted in FIGS. 3A and 3B. In this embodiment, catheter 10b is straight and suture 24b is attached to the distal end of the catheter at 26 and passes into the hollow interior of the catheter through hole 27. Thus, when suture 24b is drawn proximally, a J-curve 29 is formed in the distal end of the catheter, as depicted in FIG. 3B.

Returning to FIG. 1, an optional stress relief sleeve 28 is mounted about the rear portion 30 of proximal end 12 to facilitate handling of the catheter. Additionally, a hub 32 is attached to the stress relief sleeve (or directly to the catheter, if no stress relief sleeve is present) to facilitate attachment of the catheter to appropriate drainage devices (not shown).

End 34 of suture 24 is attached internally to the proximal end of the catheter by molding, gluing, welding or otherwise attaching that end of the suture into the interstitial space between hub 32 and stress relief sleeve 28 (or directly to the catheter, if no strain relief sleeve is present). Suture 24 is then passed through the hollow interior of the catheter to distal end 14 thereof, where it emerges through a hole 36.

The suture re-enters the catheter through a hole 35 in the restraining portion of the catheter and returns by way of the interior of the catheter to a point adjacent the proximal end of the catheter, where it emerges from suture exit 40.

An annular latex sleeve 42 covers the outer surface of the catheter near its proximal end. Latex sleeve 42, which covers suture exit 40, is pierced by the suture which emerges therefrom with a sufficient leader 46 for handling by the physician while using the catheter in a medical procedure. Due to the self-sealing properties of the latex, a tight seal to the outer surface of the suture is obtained and leakage of liquids and gases from the catheter is minimized.

Art annular silicone sheath 50 is positioned just distal to the latex sleeve. Sheath 50 is shown in a rolled up position in FIGS. 1 and 5A, with an integral preformed annular silicone ring 52 formed in the silicone sheath at its proximal end. The preformed ring helps manipulate the sheath, as described below. Thus, once the suture is drawn to the desired position (as discussed in more detail below), silicone sheath 50 is rolled over latex sleeve 42 to secure the suture into place between the inner surface of the sheath 50 and the outer surface of the sleeve 42. As noted earlier, sheath 50 serves not only to lock the suture in place but also to further minimize leakage and, for those individuals sensitive to latex, to minimize allergic reactions in the patient.

The flexible catheter of the invention may be inserted over a guidewire or by direct puncture using a trocar styler. Guidewire insertion proceeds as illustrated in part by FIGS. 4A and 4B.

Figure 4B:
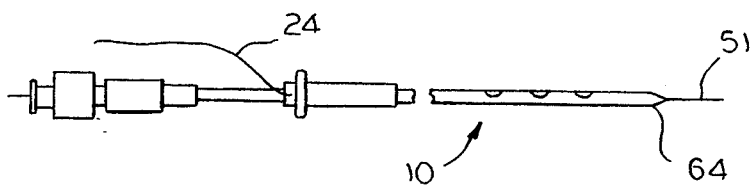

First, a drainage site is selected and prepared using standard techniques, a guidewire 51 is inserted into the drainage site through a needle and the tract is dilated. Next a stiffening cannula 60 is inserted into catheter 10 while it is straightened ahead of the advancing cannula. Once the stiffening cannula is in place, as shown in FIG. 4B, the cannula is locked into catheter hub 32. The resulting catheter/cannula assembly is advanced over the guidewire into the site.

Next, the stiffening cannula is unlocked and the catheter advanced while the cannula is held stationary. The stiffening cannula and guidewire are then removed so that the restraining means (pigtail 62) returns to its original shape (FIG. 4A). The distal tip of the catheter 64 is then moved into place in accordance with the invention by pulling back on suture 24 while monitoring under fluoroscopy until the pigtail is secured. The catheter is then attached to an appropriate drainage device and fluid is drained by suction or gravity.

Figure 5A:
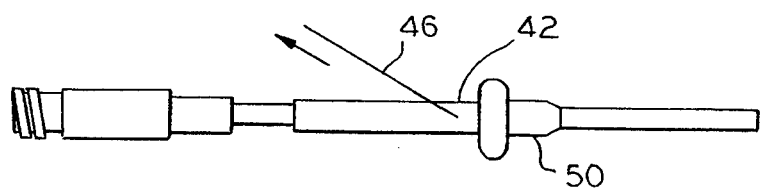
FIGS. 5A, 5B and 5C are partial elevation views of the catheter of the invention, illustrating the use of the locking of a suture leader.
Figure 5B:
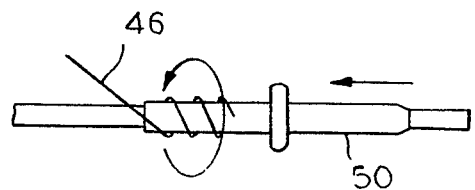
Figure 5C:
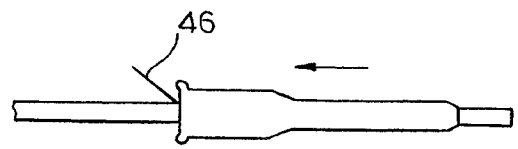

Turning now to FIG. 5A, silicone sheath 50 is shown just before suture leader 46 is to be locked in place. As seen in FIG. 5B, in order to enhance the strength of the lock, suture leader 46 is wound around latex sleeve 42 several times after which the silicone sheath 50 is unrolled proximally to removably secure the suture (FIGS. 1A and 5C). The suture can be then tied into a knot and the excess suture cut and discarded. The silicone sheath is then unrolled proximally the rest of the way so that the end of the suture is completely covered.

Figure 6A:
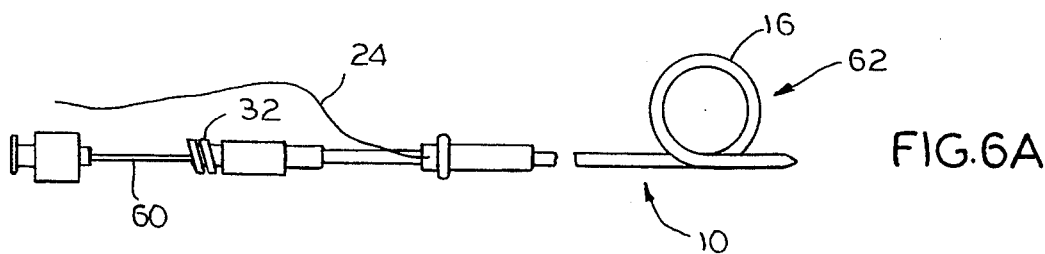
FIGS. 6A, 6B and 6C are partial elevation view of the catheter of the invention, illustrating the use of a stiffening cannula and a trocar styler.
Figure 6B:
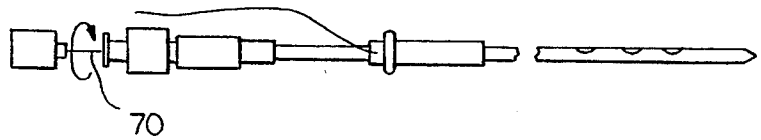
Figure 6C:
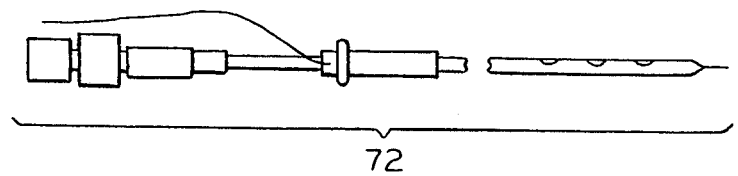

When a direct puncture technique is used, as illustrated in FIGS. 6A–C, the drainage site is selected and prepared using standard techniques, the stiffening cannula 60 is inserted while straightening the catheter ahead of the cannula, (as described above), and the stiffening cannula is locked into catheter hub 32. Then, a trocar styler 70 is advanced into place and locked into the hub of the stiffening cannula (FIG. 6B). The resulting catheter/cannula/trocar styler assembly 72 is then advanced into the site and the trocar styler removed. If desired, a guidewire may then be inserted to aid in placement.

Next, the stiffening cannula is unlocked and the catheter advanced while the cannula is held stationary whereupon the stiffening cannula and guide wire are removed. Then, the distal tip of pigtail 62 is positioned by pulling back on suture leader 46 and locking it in place, as described above. The catheter is then attached to appropriate drainage device and fluid is drained by suction or gravity.

Once the drainage procedure is completed and the catheter is to be removed, the drainage device is disconnected from the catheter and silicone sheath 50 is rolled back exposing the suture exit site on the latex sleeve. The suture can then be cut and/or untied thereby unlocking the pigtail.

The catheter may now be gently pulled from the cavity. If access is to be maintained, an appropriate guide wire (not shown) may be used to assist in removal and subsequent placement of another catheter.

While the present invention is described above in connection with specific embodiments, the invention is intended to cover all alternatives, modifications or equivalents that may be included within its sphere and scope, as defined by the appended claims.

What we claim is:

1. A locking catheter system comprising:
   a flexible catheter having a restraining portion at its distal end;
   means, extending from the restraining portion to the proximal end of the catheter, for drawing the restraining portion toward the proximal end; and
   means, at the proximal end of the catheter, for removably attaching the drawing means to the catheter, said attaching means comprising a self-sealing sleeve covering a portion of the proximal end of the catheter and an elastomeric sheath sized to fit over the self-sealing sleeve, a portion of said drawing means for positioning along the self-sealing sleeve, said portion of said drawing means restrained when the elastomeric sheath is drawn over the self-sealing sleeve.

2. The locking catheter of claim 1 in which the restraining means is a preformed curve in the distal end of the catheter.

3. The locking catheter of claim 2 in which the preformed curve is in a pigtail shape.

4. The locking catheter of claim 2 in which the preformed curve is a malecot rib.

5. The locking catheter system of claim 1 in which the drawing means is a flexible filament.

6. The locking catheter system of claim 5 in which the flexible filament is non-woven and non-porous.

7. The locking catheter system of claim 1 wherein the drawing means comprises a flexible filament positioned, in part, within the distal end of the flexible catheter to emerge from the proximal end thereof, below the self-sealing sleeve.

8. The locking catheter system of claim 1 in which the drawing means comprises a flexible filament which is fixed to the proximal end of the catheter, passing therefrom through the interior of the catheter to emerge through a hole near the distal end of the catheter, whereupon it re-enters the interior of the catheter through another, distally located opening and passes through the interior of the catheter to emerge through a suture exit in the self-sealing sleeve.

9. The locking catheter of claim 8 wherein the latex sleeve seals along the outer surface of the drawing means where it passes therethrough.

10. The locking catheter of claim 1 in which the self-sealing sleeve is made of latex.

11. The locking catheter of claim 1 in which the elastomeric sheath is made of silicone.

12. The locking catheter system of claim 1 in which the elastomeric sheath encapsulates the self-sealing sleeve.

13. The locking catheter of claim 12 in which the elastomeric sheath is adapted to be rolled up into an annular ring at the distal end of the self-sealing sleeve when in an unrestraining closed position and rolled out over the self-sealing sleeve when in a restraining position.

14. The locking catheter of claim 1 in which the elastomeric sheath includes an integral annular portion at its proximal end.

15. A locking catheter system comprising:
a flexible catheter having a restraining portion at its distal end;
a flexible filament, extending from the restraining portion to the proximal end of the catheter, for drawing the restraining portion toward the proximal end; and
means, at the proximal end of the catheter, for removably attaching the flexible filament;
said attaching means comprising a self-sealing latex sleeve for covering a portion of the proximal end of the catheter and a silicone sheath sized to fit over the latex sleeve, a portion of the flexible filament positioned along the latex sleeve and held in place by drawing the silicone sheath over the latex sleeve.

16. The locking catheter of claim 15 in which the curved portion is in the shape of a malecot rib.

17. The locking catheter of claim 15 in which the curved portion is in the shape of a J-curve.

18. The locking catheter system of claim 15 in which the drawing means is attached to the proximal end of the catheter by molding, gluing, welding or other suitable means.

19. The locking catheter system of claim 15 in which the silicone sheath includes an integral preformed annular silicon ring, attached to the silicon sheath at its proximal end.

* * * * *